(12) United States Patent
Pierce et al.

(10) Patent No.: US 10,386,278 B2
(45) Date of Patent: Aug. 20, 2019

(54) SYSTEMS AND METHODS FOR A MULTI-CHAMBERED SAMPLER

(71) Applicant: Polymer Technology Systems, Inc., Indianapolis, IN (US)

(72) Inventors: Jeffrey A. Pierce, Redwood City, CA (US); Bao Phan, San Jose, CA (US); Urs A. Ramel, Modesto, CA (US)

(73) Assignee: Polymer Technology Systems, Inc., Whitestown, IN (US)

( * ) Notice: Subject to any disclaimer, the term of this patent is extended or adjusted under 35 U.S.C. 154(b) by 88 days.

(21) Appl. No.: 15/596,946

(22) Filed: May 16, 2017

(65) Prior Publication Data
US 2017/0336305 A1 Nov. 23, 2017

Related U.S. Application Data

(60) Provisional application No. 62/337,557, filed on May 17, 2016.

(51) Int. Cl.
*G01N 1/38* (2006.01)
*B01L 3/00* (2006.01)
(Continued)

(52) U.S. Cl.
CPC .............. *G01N 1/38* (2013.01); *B01F 3/0865* (2013.01); *B01F 11/0005* (2013.01); *B01F 13/0022* (2013.01); *B01F 15/0087* (2013.01); *B01F 15/0206* (2013.01); *B01F 15/0212* (2013.01); *B01L 3/502* (2013.01); *B01F 2215/0034* (2013.01); *B01F 2215/0037* (2013.01); *B01L 2200/026* (2013.01); *B01L 2200/16* (2013.01); *B01L 2300/044* (2013.01); *B01L 2300/0672* (2013.01); *B01L 2300/087* (2013.01); *B01L 2300/0832* (2013.01);
(Continued)

(58) Field of Classification Search
CPC .............. B01F 11/0005; B01F 13/0022; B01F 15/0087; B01F 15/0206; B01F 15/0212; B01F 2215/0034; B01F 2215/0037; B01F 3/0865; B01L 2200/026; B01L 2200/16; B01L 2300/044; B01L 2300/0672; B01L 2300/0832; B01L 2300/0838; B01L 2300/0861; B01L 2300/0867; B01L 2300/087; B01L 3/502; G01N 1/38
See application file for complete search history.

(56) References Cited

U.S. PATENT DOCUMENTS 8,110,397 B2 * 2/2012 Green ................. B01F 15/0205
　　　　　　　　　　　　　　　　　　　　　　　435/287.6
2001/0039058 A1* 11/2001 Iheme ................... B01L 3/0275
　　　　　　　　　　　　　　　　　　　　　　　436/180

(Continued)

*Primary Examiner* — Jennifer Wecker
(74) *Attorney, Agent, or Firm* — Haynes and Boone, LLP

(57) ABSTRACT

A system for mixing a sample with a combined buffer includes a sampler body, the sampler body including a first reservoir and a second reservoir. The system further includes a first separator forming a first enclosure with the sampler body for the first reservoir. The system further includes a second separator forming a second enclosure with the sampler body for the first reservoir. The system further includes a third separator, in conjunction with the second separator, forming a third enclosure and a fourth enclosure, respectively, both in conjunction with the sampler body, for the second reservoir.

26 Claims, 9 Drawing Sheets

(51) Int. Cl.
  *B01F 3/08*   (2006.01)
  *B01F 15/00*  (2006.01)
  *B01F 13/00*  (2006.01)
  *B01F 15/02*  (2006.01)
  *B01F 11/00*  (2006.01)

(52) U.S. Cl.
  CPC .................. *B01L 2300/0838* (2013.01); *B01L 2300/0861* (2013.01); *B01L 2300/0867* (2013.01)

(56) References Cited

U.S. PATENT DOCUMENTS

| | | | | |
|---|---|---|---|---|
| 2005/0196872 | A1* | 9/2005 | Nguyen | B01F 5/0646 436/174 |
| 2006/0194207 | A1* | 8/2006 | Mitani | B01L 3/502 435/6.13 |
| 2009/0308184 | A1* | 12/2009 | Blekher | A61B 5/1411 73/864.63 |
| 2011/0130740 | A1* | 6/2011 | Levy | A61J 1/05 604/403 |
| 2017/0176302 | A1* | 6/2017 | Bearinger | G01N 1/38 |

\* cited by examiner

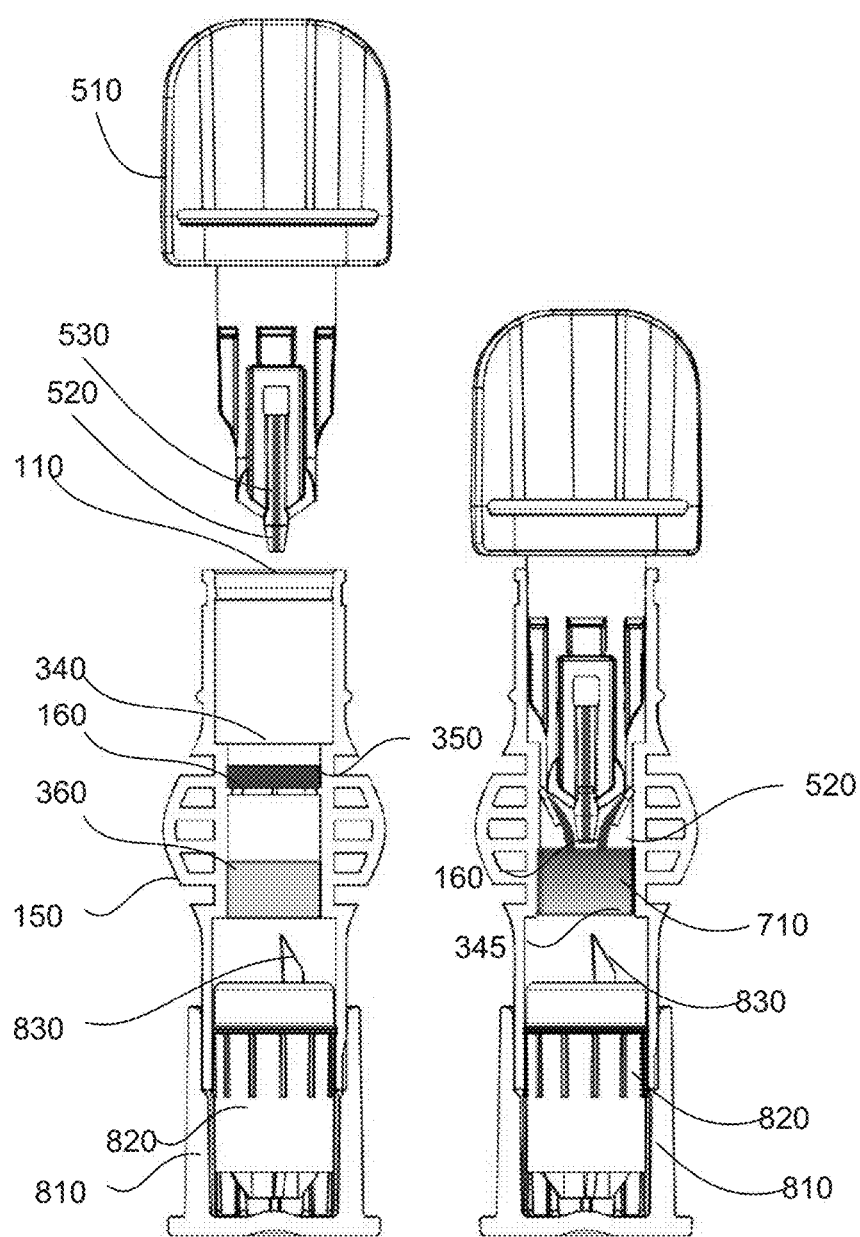
*FIG. 8A*  *FIG. 8B*

Shake Sampler Assembly

Ready for Dispense

SYSTEMS AND METHODS FOR A MULTI-CHAMBERED SAMPLER

CROSS-REFERENCE TO RELATED APPLICATIONS

This application claims the benefit of Provisional Application No. 62/337,557 filed on May 17, 2016, titled "Systems and Methods For A Multi-Chambered Sampler" the entire disclosure of which is hereby incorporated by reference.

BACKGROUND

Systems that provide for point-of-care testing of analytes are important for doctors, health professionals, and consumers. Point-of-care testing may allow for rapid results that replicate or approach the accuracy and precision available for laboratory testing. One type of point-of-care testing relies on lateral flow test strips and the use of antibodies and markers in order to determine the concentration of various analytes. As part of such a lateral flow assay, a premix step with a buffer or other reagents may be useful. Instead of providing a user in a point-of-care setting with test tubes and a vial or reagent, a "sampler" may be provided that receives a sample and includes a premixed reagent (in many cases, a buffer). The sampler then may be used to readily apply the sample to a lateral flow test strip. This greatly increases the usability of the system for consumers and other health professionals, since no test tubes are required. One downside of such samplers is that they may contain only one compartment, so if multiple reagents or substances are used, they may need to be premixed and stored in the sampler together. This may decrease the effective life of such reagents.

SUMMARY

In one embodiment, a system for mixing a sample with a combined buffer includes a sampler body, the sampler body including a first reservoir and a second reservoir. The system further includes a first separator forming a first enclosure with the sampler body for the first reservoir. The system further includes a second separator forming a second enclosure with the sampler body for the first reservoir. The system further includes a third separator, in conjunction with the second separator, forming a third enclosure and a fourth enclosure, respectively, both in conjunction with the sampler body, for the second reservoir. Optionally, the first and third separators are foil. Alternatively, the second separator is a septum. In one alternative, the first reservoir includes a first buffer and the second reservoir includes a second buffer. In another alternative, the system further includes a blood collector, the blood collector including a piercing projection, and the blood collector shaped to mate with the sampler body, such that when the blood collector is inserted into the sampler body at an aperture in the sampler body, liquid cannot escape from the combination of the sampler body and the blood collector. Alternatively, upon insertion of the blood collector into the sampler body, the piercing projection of the sampler body pierces the first and second separators. Optionally, the sampler body includes a capillary tube that holds the sample. Alternatively, upon insertion of the blood collector into the sampler body, the first and second buffers mix with the sample. Optionally, the sampler body includes a cylindrical cavity that houses the first and second reservoirs. In one configuration, the septum provides one pound of force resistance to piercing. In another configuration, the septum has four equal quadrants joined by a thin connector material. Optionally, the septum is molded plastic. Alternatively, the four equal quadrants are thicker that the thin connector material.

In one embodiment, a method for mixing a sample with a combined buffer includes providing a sampler body. The sampler body includes a first reservoir and a second reservoir. The sampler body further includes a first separator forming a first enclosure with the sampler body for the first reservoir. The sampler body further includes a second separator forming a second enclosure with the sampler body for the first reservoir. The sampler body further includes a third separator, in conjunction with the second separator, forming a third enclosure and a fourth enclosure, respectively, both in conjunction with the sampler body, for the second reservoir. The method further includes providing a blood collector, the blood collector including a piercing projection, and the blood collector shaped to mate with the sampler body, such that when the blood collector is inserted into the sampler body at an aperture in the sampler body, liquid cannot escape from the combination of the sampler body and the blood collector. The method further includes inserting the blood collector into the sampler body; advancing the blood collector and breaking the first separator; and advancing the blood collector and breaking the second separator. Optionally, the first reservoir includes a first buffer and the second reservoir includes a second buffer. In one alternative, the method further includes mixing the first and second buffers; and mixing a sample held in the blood collector with the first and second buffers by agitating the combined sampler body and blood collector. Optionally, the first and third separators are foil. Alternatively, the second separator is a septum. Optionally, the sampler body includes a capillary tube that holds the sample.

In another configuration, the septum has four equal quadrants joined by a thin connector material. Optionally, the septum is molded plastic. Alternatively, the four equal quadrants are thicker that the thin connector material.

BRIEF DESCRIPTION OF THE DRAWINGS

FIGS. 8A and 8B show another view of the insertion of the blood collector into the sampler body;

DETAILED DESCRIPTION

Figure 1:
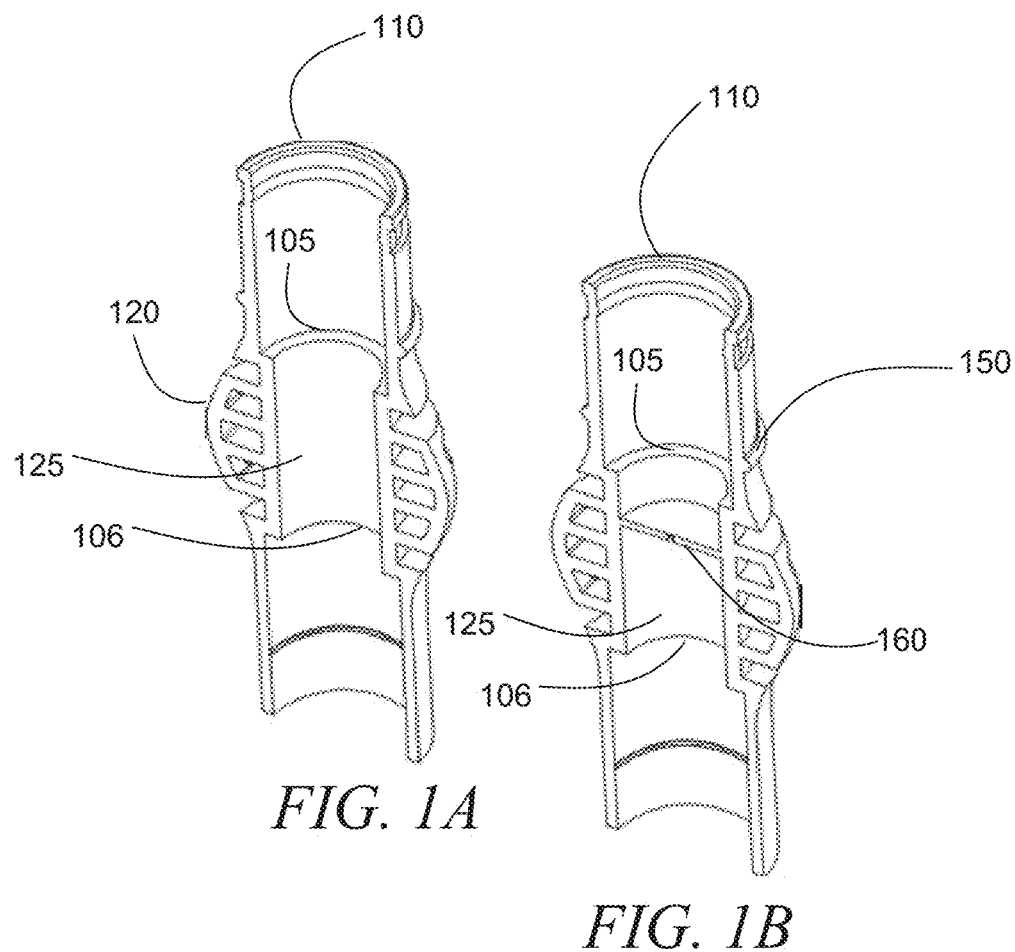
FIG. 1A shows one embodiment of a single chamber sampler body.
FIG. 1B shows an embodiment of a double chamber sampler body having a septum or other separator in the sampler body.

Certain terminology is used herein for convenience only and is not to be taken as a limitation on the embodiments of the systems and methods for a multi-chambered sampler. In the drawings, the same reference letters are employed for designating the same elements throughout the several figures. In many embodiments, a multi-chambered sampler uses a first separator and a second separator to hold two compartments of reagents. In many embodiments, a sample collector is used to penetrate both the first and second separators. This allows for the mixing of a sample in the sample collector with both reagents.

In some point-of-care tests, a required buffer is stable in the short term (hours), but unstable in the longer term (weeks to months). These point-of-care tests typically involve a sampler, including a blood collector, a sampler body, and a sampler base, and a test cartridge or test strip for receiving a sample mixed in the sampler. In order to achieve long-term stability of the buffer and hence the product, the buffer should be prepared in two stable fractions and those fractions mixed to form the active buffer just prior to use. Embodiments of the multi-chambered sampler address the issue of managing the two stable fractions of the proposed buffer while continuing to be able to offer customers an easy-to-use sampler body system. The goal is to achieve a sampler design that would keep the unstable fractions separated until needed; then the standard action of the user inserting the blood-filled blood collector into the sampler body and subsequently shaking it would automatically mix the buffer fractions together with the blood, and the combination then could be dispensed into the test cartridge in the standard fashion.

Therefore, embodiments of a sampler are described herein that provide for two compartments for holding two buffers that are combined at the time of usage. This sampler is easy to use and merely requires the user to insert a mated blood collection device into the sampler.

FIG. 1A shows one embodiment of a sampler body. Sampler body 120 includes an upper end aperture 110 for the insertion of a sample collector. As shown, the central storage area 125 is a single piece. In contrast, FIG. 1B shows an embodiment of a sampler body having a septum 160 or other separator in sampler 150. This effectively divides the central reagent storage area with a septum that later can be broken by the blood collection device. A molded dual chamber sampler body contains a septum 160 that is strong enough to keep the two solutions apart during storage, but weak enough that the mechanical action of inserting the blood collector into the sampler body breaks the septum and allows the solutions to mix. FIG. 1A shows a view of a sampler body 120 cross-section with a single central chamber 125 (after the foil staking process), and FIG. 1B shows a view of a sampler body 150 cross-section with a single septum 160 splitting central chamber 125 into two chambers (after the foil staking process). The foil staking process will be explained in the subsequent figures; however, the top portion of central chamber 125 is typically foil covered to seal the reagent in the central chamber 125. In both embodiments, the sampler body 150 includes a upper foil sealing surface 105 and a lower foil sealing surface 106. The blood collector pierces this foil.

Figure 2:
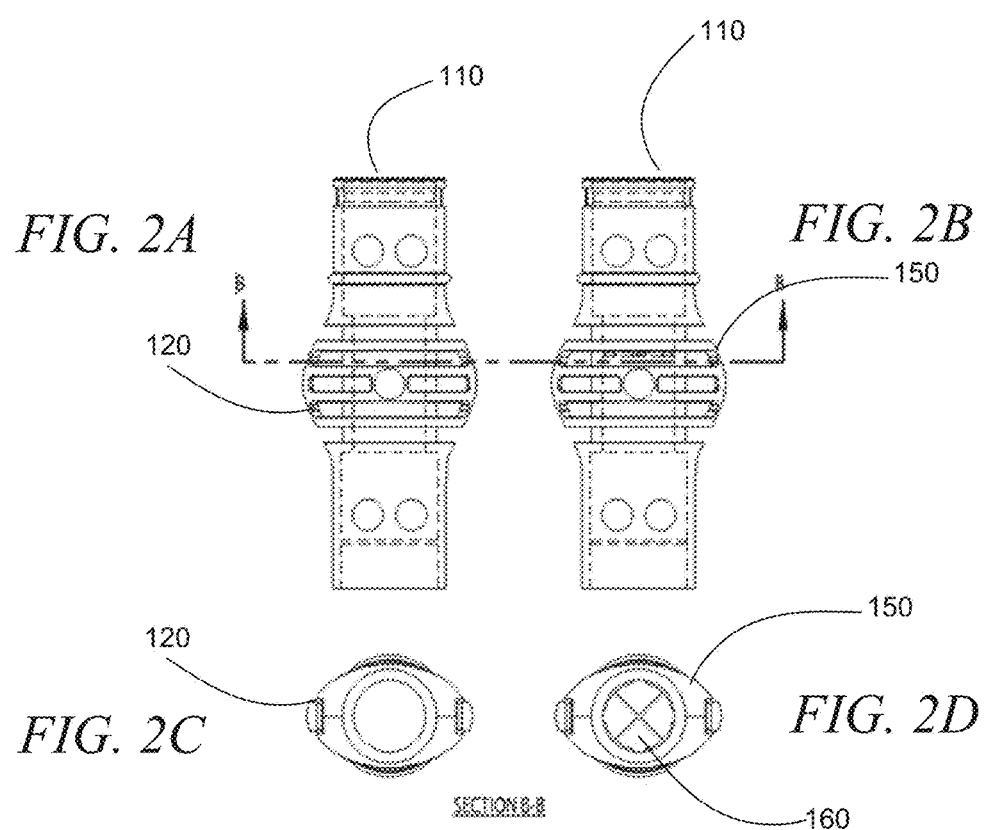
FIGS. 2A and 2C show a single chamber sampler body and a cross-section of sampler body 120 along cross-section line B, respectively.
FIGS. 2B and 2D show a double chamber sampler body and a cross-section of sampler body 150, along cross-section line B, respectively.

FIGS. 2A and 2C show a sampler body 120 and a cross-section of sampler body 120, along cross-section line B, respectively. FIGS. 2B and 2D show a sampler body 150 and a cross-section of sampler body 150, along cross-section line B, respectively. Here, septum 160 is visible. Septum 160 may be formed from a variety of materials such as plastics, foils, and other materials. As shown, septum 160 includes four equal sections that are separated by a thin joint of material that may easily rip and break when the blood collector is inserted. In the embodiment shown, septum 160 may be made of plastic as well as other materials.

Figure 3:
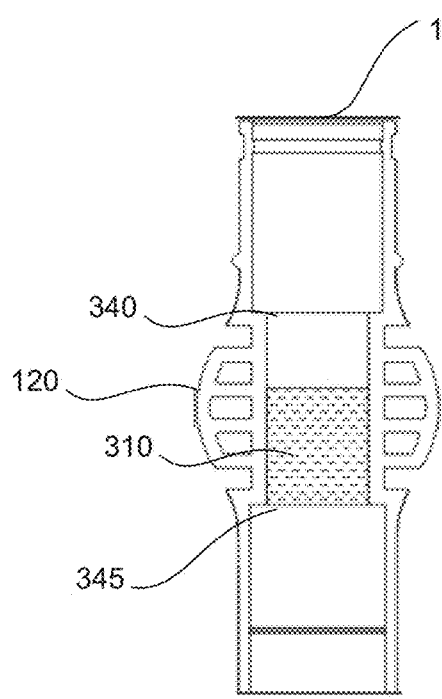
FIG. 3 shows an embodiment of a sampler body with a single buffer-filled chamber formed by foil heat staked ends.
Figure 4:
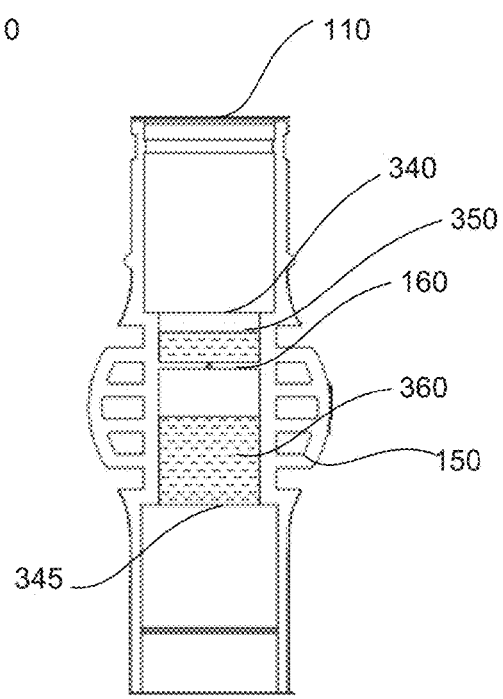
FIG. 4 shows an embodiment of a sampler body with two buffer-filled chambers formed from molded-in septum and foil heat staked ends.

FIG. 3 shows an embodiment of a sampler body 120 with single buffer-filled chamber formed by foil heat staked ends. FIG. 4 shows an embodiment of a sampler body 150 with two buffer-filled chambers formed from molded-in septum and foil heat staked ends. As is shown, sampler body 120 includes a top foil closure 340 and a bottom foil closure 345. A reagent 310 (in many cases, a buffer) is stored in the chamber between the top foil closure 340 and the bottom foil closure 345. In sampler body 150, a first reagent 350 is stored between a top foil closure 340 and the septum 160. A second reagent 360 is stored between the septum 160 and the bottom foil closure 345. Although the septum and closures are described as having specific properties, alternative materials and closures may be used in some embodiments. For instance, plastics, coated papers, and other materials that may be made thin enough to pierce may be utilized for the foil closures and, similarly, the same materials or foil may be used for the septum.

Figures 5A, 5B, 5C:
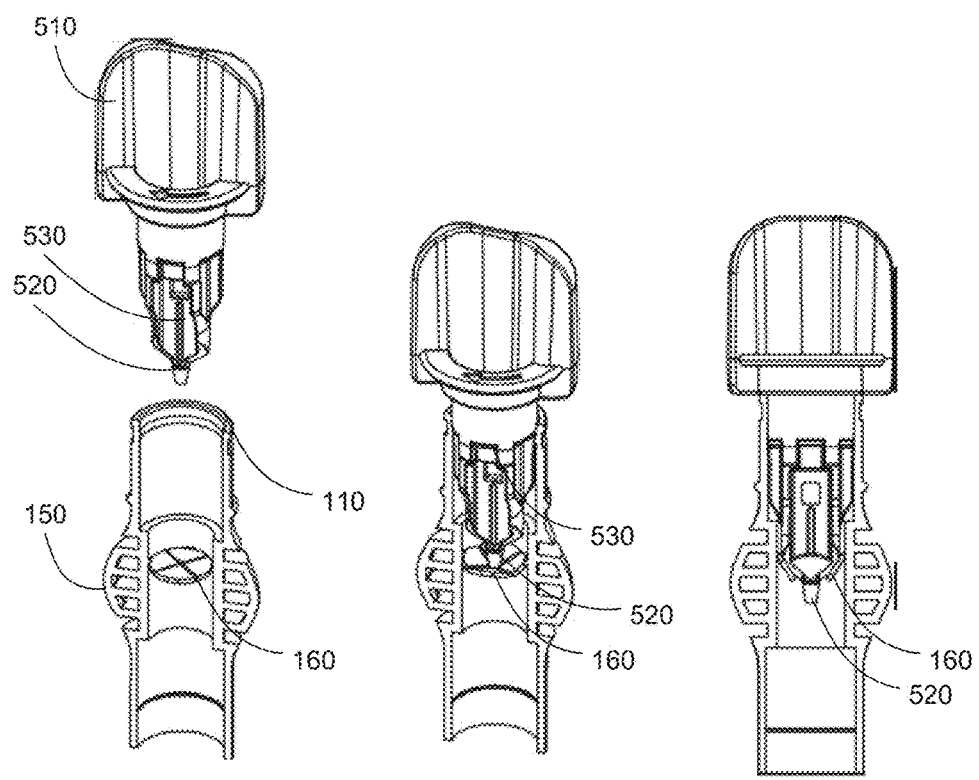
FIGS. 5A, 5B and 5C show the progressive insertion of the blood collector into the septum-containing sampler body, showing the opening of the septum through the insertion force of the blood collector.

FIGS. 5A-5C show the progressive insertion of a blood collector into a septum-containing sampler body showing the opening of the septum through the insertion force of the blood collector. Current insertion force of the blood collector is about five to ten pounds. Expected yield force of molded-in septum is about one pound force, so the user will be unaware of the added complexity of this sampler design. In FIG. 5A, a blood collector 510 is used to retrieve a sample, typically a blood sample resulting from a finger prick. Blood collector 510 includes a piecing tip 520 and a capillary tube 530 that holds a sample. As shown, blood collector 510 is aligned with the top aperture 110 of sampler body 150 that includes septum 160. FIG. 5B shows the sampler body 150 advanced to the septum 160. Because of the venting mechanism 530, the force of air attempting escape should be at a minimum. Blood collector 510 mates precisely with sampler body 150 such that no liquid will escape during insertion as the foil and septum 160 are penetrated. FIG. 5C shows the piercing projection 520 advanced through the septum 160.

Figure 6:
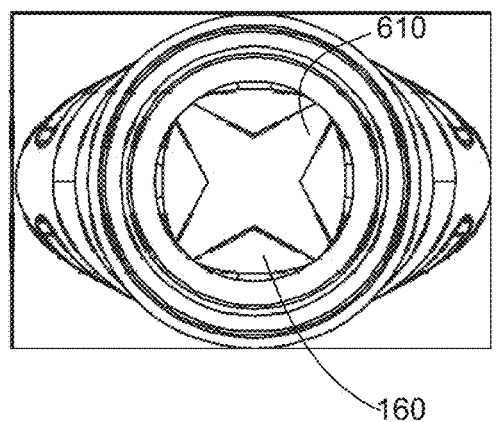
FIG. 6 shows one view of an embodiment of the septum after the piercing projection has broken it.

FIG. 6 shows one view of an embodiment of the septum 160 after the piecing projection 520 has broken it. Although some material may remain, the fluid flow past septum 160 should be largely uninhibited after piercing.

Figure 7:
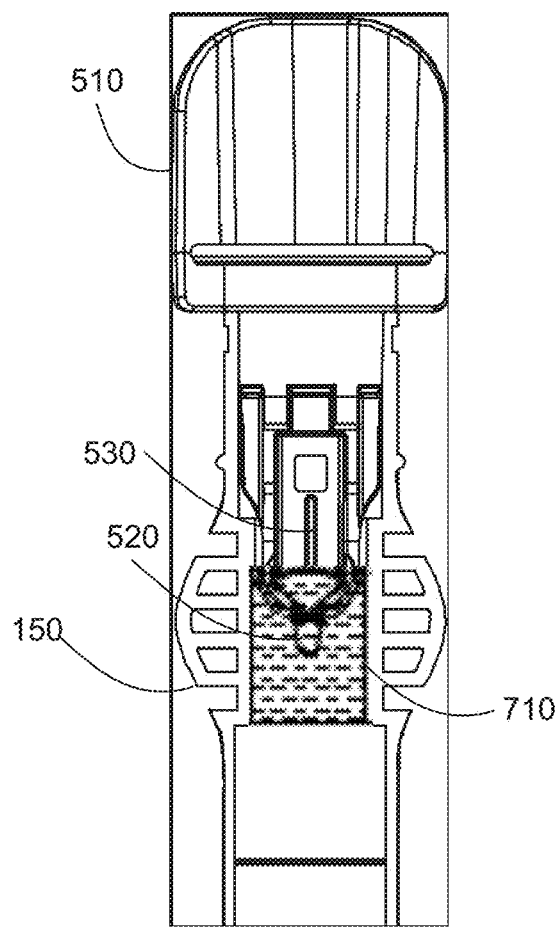
FIG. 7 shows the blood collector fully inserted into the sampler body.

FIG. 7 shows blood collector 510 fully inserted into sampler body 150, breaking the heat staked top foil seal as well as molded-in septum 160, allowing fluids in both chambers to mix into a combined reagent 710.

FIGS. 8A and 8B show another view of the insertion of blood collector 510 into sampler body 150. As shown, blood collector 510 includes a piercing projection 520 and a capillary tube 530 containing a sample. The blood collector 510 aligns with the aperture 110 in sampler body 150 and may be inserted. Upon insertion, piercing projection 520 breaks foil 340 and septum 160, allowing the first reagent 350 and the second reagent 360 to mix into reagent mixture 710. Bottom foil 345 holds the mixture in the central chamber until the mixed sample is to be applied to a cassette or test strip. Also visible in these figures is the sampler base 810. The sampler base 810 includes the sampler plunger 820 and the piercing projection 830 for piercing bottom foil 345 to release the sample onto a test strip after mixing.

Figures 9A, 9B:
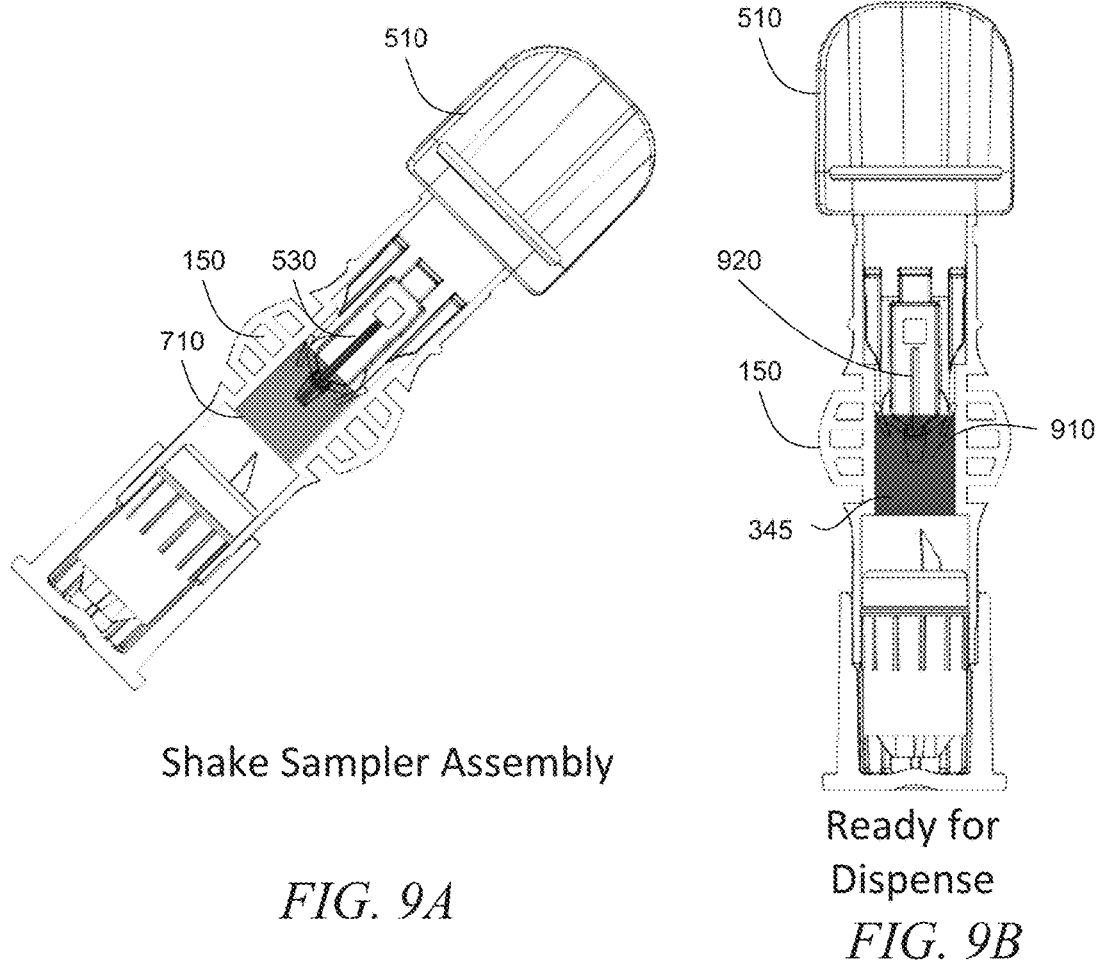
FIG. 9A shows the sampler body oriented to mix the blood sample with the reagent mixture.
FIG. 9B shows another view of the insertion of the blood collector into the sampler body.

FIGS. 9A and 9B show the next steps in the sampling process. In FIG. 9A, the combined sampler body 150 and blood collector 510 are sealed together by virtue of their mated fit and may be agitated in order to mix the blood sample in capillary tube 530 with the reagent mixture. In FIG. 9B, the blood sample has been mixed and capillary tube 920 is largely empty. The combined blood sample and reagent mixture 910 then is ready to be applied to a cassette or test strip by piercing the foil 345 according to a different procedure not addressed herein. In this way, the two reagents may be kept separate and combined in a seamless fashion from the point of view of the user. This improves the shelf life of the device by preventing the reagents (buffers) from degrading due to their combination. In some alternatives, additional separation layers may be added. The addition of more separation layers may increase the number of compartments provided in the central chamber. Generally, the additional separation layers or septums should be within the range of the blood sampler body such that they may be pierced during insertion; however, they cannot be placed too high towards the aperture, since this will result in the leaking/pushing out of liquid when the blood sampler body is inserted.

Figure 10A:
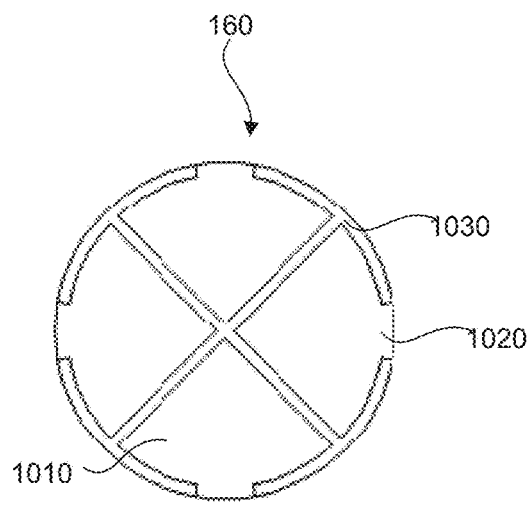
FIGS. 10A and 10B show views of an embodiment of a septum.
Figure 10B:
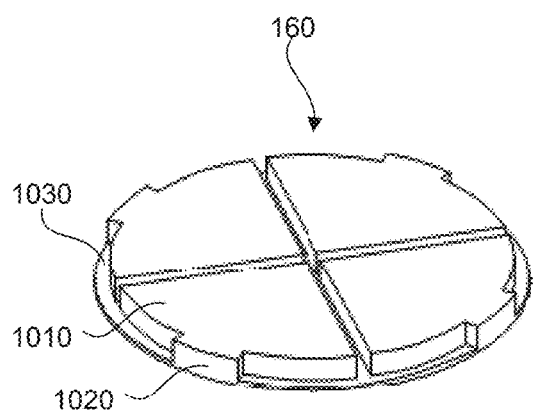
Figure 11A:
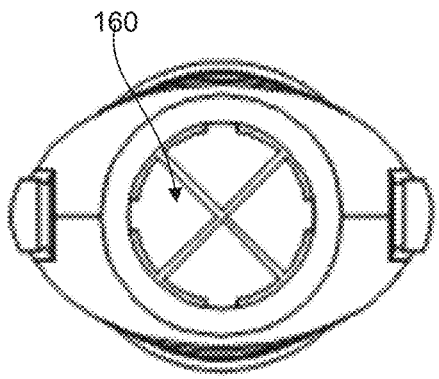
FIG. 11A shows the septum of FIG. 10A in a sampler body.
Figure 11B:
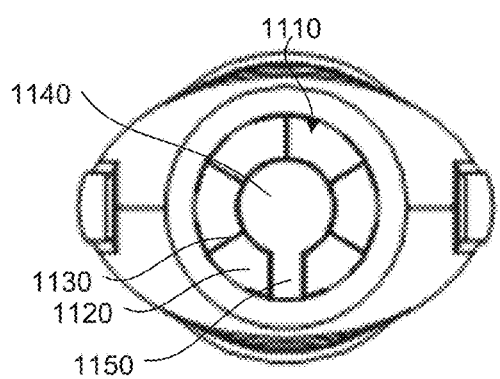
FIG. 11B shows an alternative embodiment of a septum.

FIGS. 10A and 10B show views of the septum 160. Septum 160 includes a hinge feature 1020, breakaway sections 1010, and tearoff sections 1030. In some embodiments, breakaway sections are 0.020 inches thick and tearoff sections are 0.003 inches thick. This is purely exemplary. In some embodiments, breakaway sections are tenths of an inch thick and tearoff sections are hundredths of an inch thick. As above, this is merely an example. The point of this is to provide areas where the septum may rip more easily to provide a more regular breaking pattern. FIG. 11A shows septum 160 in the sampler body. FIG. 11B shows an alternative embodiment of a septum 1110. Septum 1110 includes panel sections 1120, center section 1140, connection section 1150, and tearaway sections 1130 that separate the panels, center, and connection. Numerous other geometries will occur to those of ordinary skill in the art based on the teaching of this disclosure.

While specific embodiments have been described in detail in the foregoing detailed description and illustrated in the accompanying drawings, it will be appreciated by those skilled in the art that various modifications and alternatives to those details could be developed in light of the overall teachings of the disclosure and the broad inventive concepts thereof. It is understood, therefore, that the scope of this disclosure is not limited to the particular examples and implementations disclosed herein but is intended to cover modifications within the spirit and scope thereof as defined by the appended claims and any and all equivalents thereof.

What is claimed as new and desired to be protected by Letters Patent of the United States is:

1. A system for mixing a sample with a combined buffer, the system comprising:
    a sampler body, the sampler body including a first reservoir and a second reservoir;
    a first separator forming a first enclosure with the sampler body for the first reservoir;
    a second separator forming a second enclosure with the sampler body for the first reservoir;
    a third separator, in conjunction with the second separator, forming a third enclosure and a fourth enclosure, respectively, both in conjunction with the sampler body, for the second reservoir,
    a first piercing element configured to pierce the first and second separators; and
    a second piercing element configured to pierce the third separator.

2. The system of claim 1, wherein the first and third separators are foil.

3. The system of claim 2, wherein the second separator is a septum.

4. The system of claim 3, wherein the first reservoir includes a first buffer and the second reservoir includes a second buffer.

5. The system of claim 4, further comprising:
    a blood collector, the blood collector including the first piercing projection, the blood collector shaped to mate with the sampler body, such that when the blood collector is inserted into the sampler body at an aperture in the sampler body, liquid cannot escape from the combination of the sampler body and the blood collector.

6. The system of claim 5, wherein upon insertion of the blood collector into the sampler body, the first piercing projection of the sampler body pierces the first and second separators.

7. The system of claim 6, wherein the sampler body includes a capillary tube that holds the sample.

8. The system of claim 7, wherein upon insertion of the blood collector into the sampler body, the first and second buffers mix with the sample.

9. The system of claim 8, wherein the sampler body includes a cylindrical cavity that houses the first and second reservoirs.

10. The system of claim 9, wherein the septum provides one pound of force resistance to piercing.

11. The system of claim 9, wherein the septum has four equal quadrants joined by a thin connector material.

12. The system of claim 11, wherein the septum is molded plastic.

13. The system of claim 12, wherein the four equal quadrants are thicker that the thin connector material.

14. A method for mixing a sample with a combined buffer, the method comprising:
    providing a sampler body, the sampler body including:
        a first reservoir and a second reservoir;
        a first separator forming a first enclosure with the sampler body for the first reservoir;
        a second separator forming a second enclosure with the sampler body for the first reservoir; and
        a third separator, in conjunction with the second separator, forming a third enclosure and a fourth enclosure, respectively, both in conjunction with the sampler body, for the second reservoir;
    providing a blood collector, the blood collector including a first piercing projection, the blood collector shaped to mate with the sampler body, such that when the blood collector is inserted into the sampler body at an aperture in the sampler body, liquid cannot escape from the combination of the sampler body and the blood collector;
    inserting the blood collector into the sampler body;

advancing the blood collector and breaking the first separator with the first piercing projection;

advancing the blood collector and breaking the second separator with the first piercing projection;

connecting a sampler base to the sampler body, the sampler base including a plunger and a second piercing projection; and advancing the sampler base and breaking the third separator with the second piercing projection.

15. The method of claim 14, wherein the first reservoir includes a first buffer and the second reservoir includes a second buffer.

16. The method of claim 14, further comprising:

mixing the first and second buffers; and mixing a sample held in the blood collector with the first and second buffers by agitating the combined sampler body and blood collector.

17. The method of claim 16, wherein the first and third separators are foil.

18. The method of claim 17, wherein the second separator is a septum.

19. The method of claim 18, wherein the sampler body includes a capillary tube that holds the sample.

20. The method of claim 19, wherein the septum has four equal quadrants joined by a thin connector material.

21. The method of claim 20, wherein the septum is molded plastic.

22. The method of claim 21, wherein the four equal quadrants are thicker than the thin connector material.

23. The system of claim 1, further comprising a sampler base connected to the sampler body, the sampler base including a plunger and the second piercing element.

24. The system of claim 5, wherein the sampler body includes opposing open ends, one end open to receive the blood collector, the other end open to release the combined buffer onto a test strip when the third separator is pierced by the second piercing element.

25. The system of claim 11, wherein the thin connector material is a weakened region of material connected to the four equal quadrants, the thin connector material breaking upon insertion of the blood collector.

26. A system for mixing a sample with a combined buffer, the system comprising:

a sampler body, the sampler body including a first reservoir and a second reservoir;

a first separator forming a first enclosure with the sampler body for the first reservoir;

a second separator forming a second enclosure with the sampler body for the first reservoir, the second separator also forming a first enclosure with the sampler body for the second reservoir;

a third separator forming a second enclosure with the sampler body for the second reservoir; and a sampler base connected to the sampler body, the sampler base including a plunger and a piercing element.

* * * * *